United States Patent [19]

Mount et al.

[11] 4,448,978

[45] May 15, 1984

[54] PROCESS FOR PREPARING MALEIC ANHYDRIDE

[75] Inventors: Ramon A. Mount; James T. Wrobleski, both of St. Louis, Mo.

[73] Assignee: Monsanto Company, St. Louis, Mo.

[21] Appl. No.: 355,936

[22] Filed: Mar. 8, 1982

Related U.S. Application Data

[63] Continuation of Ser. No. 223,659, Jan. 9, 1981, abandoned.

[51] Int. Cl.$^3$ ............................................ C07D 307/60
[52] U.S. Cl. ...................................... 549/259; 252/537
[58] Field of Search .......................................... 549/259

[56] References Cited

U.S. PATENT DOCUMENTS 3,293,268 12/1966 Bergman et al. .................... 549/259
4,227,945 9/1980 Higgins et al. ...................... 549/259

Primary Examiner—Henry R. Jiles
Assistant Examiner—Bernard Dentz
Attorney, Agent, or Firm—Wendell W. Brooks; James C. Logomasini; Arnold H. Cole

[57] ABSTRACT

In conventional procedures for the preparation of phosphorus-vanadium-oxygen catalysts, with or without promoting elements or carriers, the phosphorus compounds and vanadium compounds are mixed under conditions to form precursors. These precursors are then heated to temperatures up to 600° C. to form phosphorus-vanadium-oxygen catalysts suitable for the conversion of saturated hydrocarbons, such as butane, to maleic anhydride. The present invention employs a new phosphorus-vanadium-oxygen hydrogen intermediate composition which can be converted to the precursor. Catalysts formed from the intermediate are used, according to this invention, for the conversion of saturated hydrocarbons to maleic anhydride.

6 Claims, No Drawings

PROCESS FOR PREPARING MALEIC ANHYDRIDE

BACKGROUND OF THE INVENTION

This is a continuation of application Ser. No. 223,659 filed Jan. 9, 1981 and now abandoned.

This invention relates to a method for preparing maleic anhydride by the oxidation of hydrocarbons.

Maleic anhydride is of significant commercial interest throughout the world. It is used alone or in combination with other acids in the manufacture of alkyd and polyester resins. It is also a versatile intermediate for chemical synthesis. Significant quantities of maleic anhydride are produced each year to satisfy these needs.

The prior art teaches that vanadium catalysts are well suited to the production of maleic anhydride from hydrocarbons, and further, that vanadium catalysts with a vanadium valence between about 3.8 and 4.8 are particularly well suited for the production of maleic anhydride from saturated hydrocarbons. The prior art further teaches that phosphorus-vanadium-oxygen catalysts are particularly useful for the conversion of aliphatic hydrocarbons to maleic anhydride and discloses a number of ways of preparing such catalysts.

Many prior art procedures for the preparation of phosphorus-vanadium-oxygen catalysts teach that it is preferable to reduce the vanadium in solution to the tetravalent state. For example, these catalysts can be prepared by contacting phosphorus compounds and vanadium compounds under conditions to form the tetravalent vanadium and to form the catalyst precursor, and thereafter, calcining the resultant phosphorus-vanadium-oxygen compound.

The art has taught and is continuing to search for new methods of improving catalyst performance, any of which may, alone or in combination have commercial significance and constitute a significant advance in the art. Such improvement is an object of this invention.

SUMMARY OF THE INVENTION

Incident to this invention, a method of preparing a catalyst intermediate is provided which comprises: bringing together under reaction conditions a phosphorus compound, a vanadium compound and hydrogen iodide in the presence of water at a phosphorus to vanadium atom ratio between about 0.81 and about 1.5:1 under acidic conditions so as to dissolve the reactant compounds and provide at least 50 atom percent tetravalent vanadium and to form a phosphorus-vanadium-oxygen catalyst intermediate. The intermediate compound is a hydrate composition, which comprises phosphorus, vanadium, hydrogen and oxygen. It has a unique X-ray diffraction pattern. This hydrate composition can be partially dehydrated to yield an amorphous compound; then heated in an aqueous environment to a temperature of 120°–350° C. preferably 145°–150° C. to form a catalyst precursor; and thereafter calcined at a temperature between about 300° C. and about 600° C. to activate the precursor.

According to this invention, the catalysts prepared from this intermediate (hereafter referred to as the "catalysts" of this invention) are used to convert aliphatic hydrocarbons, both saturated and unsaturated, especially butane, to maleic anhydride by passing the hydrocarbons, mixed with an oxygen-containing gas, through the catalyst at elevated temperatures. The catalysts are prepared from the phosphorus-vanadium-oxygen intermediate compound which has a unique X-ray diffraction pattern. This intermediate compound is not obtained by prior art methods and is believed to be responsible for the improved performance of the catalysts made according to the method described. Details of the catalyst preparation, the X-ray diffraction analysis of the intermediate compound, and the use of the catalysts made via the intermediate compound to convert saturated hydrocarbons to maleic anhydride are hereafter described.

The vanadium compounds useful in the process of the present invention are those known to the art. Suitable vanadium compounds include: vanadium oxides, such as vanadium pentoxide, vanadium tetroxide, vanadium trioxide, and the like; vanadium oxyhalides, such as vanadyl chloride, vanadyl dichloride, vanadyl trichloride, vanadyl bromide, vanadyl dibromide, vanadyl tribromide, and the like; vanadium acids, such as metavanadic acid, pyrovanadic acid, and the like; and vanadium salts, such as ammonium metavanadate, vanadium sulfate, vanadium phosphate, vanadyl formate, vanadyl oxalate, and the like. However, vanadium pentoxide is preferred.

As a source of phosphorus for use in preparing the catalyst made by the process of the present invention, suitable phosphorus compounds include: phosphoric acid, such as metaphosphoric acid, orthophosphoric acid, triphosphoric acid, pyrophosphoric acid, and the like; phosphorus pentoxide, and the like; phosphorus halides, such as phosphorus oxyiodide, phosphorus pentachloride, phosphorus oxybromide, and the like; organophosphorus compounds, such as ethyl phosphate, methyl phosphate, and the like; and trivalent phosphorus compounds, such as phosphorus acid, phosphorus trichloride, phosphorus tribromide or organic phosphites, sometimes known as phosphonates, of the type such as trimethyl phosphite, triethyl phosphite, tripropyl phosphite, and the like. Mixtures of these phosphorus compounds can also be used. However, phosphoric acid, phosphorous acid and phosphorus pentoxide are preferred.

According to this invention, a vanadium compound is reacted with a phosphorus compound and hydrogen iodide is added to dissolve the starting materials, to reduce any pentavalent vanadium to tetravalent vanadium, and to maintain the vanadium in the tetravalent state.

To the medium containing the reaction product of the phosphorus compound, the vanadium compound and water, hydrogen iodide is added slowly until a blue solution is obtained indicating that a substantial amount, i.e., greater than 50 atom percent, of the vanadium is in the tetravalent state. The amount of time required to dissolve the phosphorus and vanadium compounds and to reduce a substantial amount of the vanadium to the tetravalent state to form an intermediate oxide complex varies from batch to batch depending upon the compounds used as starting materials and the temperature of the reaction medium and the speed with which HI is added. Ordinarily, the color of the solution changes to dark blue, indicating that a substantial amount of the vanadium is in the tetravalent state. Of course the solution can be analyzed to insure that most of the vanadium is in the tetravalent state.

Although any number of phosphorus compounds and vanadium compounds can be used to form the phosphorus-vanadium-oxygen hydrogen complex, the atom ratio of phosphorus to vanadium in the complex is important since it controls the phosphorus to vanadium atom ratio in the final catalyst. When the phosphorus to vanadium atom ratio is below about 0.8:1 or above about 1.5:1, the yield of maleic anhydride using the catalyst prepared by the process of the present invention is so low that it is not of commercial significance. It is preferred to maintain the phosphorus-to-vanadium atom ratio between about 1:1 and 1.2:1, say about 1.05:1.

After the intermediate compound has been formed, it may then be partially dehydrated as, for example, by drying at or above room temperature thus forming an amorphous PVO compound. This compound is then heated to a temperature above about 130° C., and preferably from about 130° C. to about 170° C. more preferably 140°–160° C. in a closed vessel in the presence of steam for a period of time between about 2 and about 4 hours, to form a catalyst precursor.

After the catalyst precursor has been formed, it may be calcined at temperatures between about 300° C. and about 600° C. to form a phosphorus-vanadium-oxygen catalyst. Techniques for calcining the catalyst precursor are known to those skilled in the art, and the catalyst precursor can be calcined in an inert gas or in air, or even in the presence of a mixture of a hydrocarbon and air, to form a suitable catalyst. After the phosphorus-vanadium-oxygen catalyst precursors have been calcined to form a phosphorus-vanadium-oxygen catalyst, the catalysts can be used to convert aliphatic hydrocarbons to maleic anhydride. However, the initial yield of maleic anhydride may be low, and if this is the case, the catalysts can be "conditioned" as known to those skilled in the art, by passing low concentrations of aliphatic hydrocarbon-in-air at low space velocities through the catalysts for a period of time before production operations begin.

THE INTERMEDIATE

The intermediate compound of this invention is a composition comprising phosphorus, vanadium, oxygen and hydrogen having the following major X-ray diffraction peaks measured using CuKα radiation in a General Electric X-ray Diffractometer, Model 5:

| Relative Intensity | d-spacing |
|---|---|
| 100 | 7.45 |
| 100 | 6.52 |
| 20 | 5.44 |
| 20 | 4.89 |
| 15 | 4.80 |
| 40 | 4.20 |
| 20 | 4.12 |
| 50 | 4.04 |
| 20 | 3.95 |
| 15 | 3.70 |
| 30 | 3.26 |
| 40 | 3.20 |
| 10 | 3.10 |
| 10 | 2.96 |
| 10 | 2.90 |
| 45 | 2.87 |
| 50 | 2.80 |
| 10 | 2.68 |
| 15 | 2.64 |
| 10 | 2.24 |
| 10 | 2.17 |
| 10 | 2.03 |
| 10 | 2.02 |
| 10 | 1.98 |

The catalyst precursor subsequently formed from the intermediate is an oxide composition comprising phosphorus, vanadium, hydrogen and oxygen typically having the following major X-ray diffraction peaks measured using CuKα radiation in a General Electric X-ray Diffractometer, Model 5:

| °2 theta (CuKα) | Relative Intensity | d-spacing |
|---|---|---|
| 15.40 | 100 | 5.75 |
| 19.60 | 100 | 4.52 |
| 21.70 | 10 | 4.10 |
| 24.20 | 60 | 3.68 |
| 27.10 | 50 | 3.29 |
| 28.70 | 20 | 3.11 |
| 30.40 | 70 | 2.94 |
| 32.10 | 20 | 2.79 |
| 33.70 | 30 | 2.66 |

Structural differences between the intermediate compound of this invention and the typical precursor can be seen from comparison of the above X-ray diffraction patterns of the two compounds.

PREPARATION OF MALEIC ANHYDRIDE

After the intermediate compound is converted to the phosphorus-vanadium-oxygen catalyst precursor, and the catalyst precursor has been calcined, the catalyst thus formed is placed in a reactor used to convert hydrocarbons to maleic anhydride. Thereafter, a hydrocarbon and air mixture can be passed through the catalyst to produce maleic anhydride.

The catalysts of the present invention are useful in a variety of reactors to convert hydrocarbons to maleic anhydride. Both fluidized bed reactors and fixed tube heat exchanger type reactors are satisfactory and the details of the operation of such reactors are well known to those skilled in the art. The reaction to convert hydrocarbons to maleic anhydride requires only passing the hydrocarbons admixed with a free-oxygen containing gas, such as air or oxygen-enriched air, through the catalyst at elevated temperatures. The hydrocarbon-air mixture is passed through the catalysts at a concentration of about 1 to about 10 mole percent hydrocarbon at a space velocity of about 100 to 3,000 cc/cc/hour and at temperatures between about 350° C. and about 600° C. to provide high maleic anhydride yields.

Maleic anhydride produced by using the process of this invention can be recovered by any number of means well known to those skilled in the art. For example, the maleic anhydride can be recovered by direct condensation or by adsorption in suitable media with subsequent separation and purification of the anhydride.

A large number of non-aromatic hydrocarbons having from 4 to 10 carbon atoms can be converted to maleic anhydride using the catalysts of the present invention. It is only necessary that the hydrocarbon contain not less than 4 carbon atoms in a straight chain. As an example, the preferred saturated hydrocarbon is butane, but isobutane which does not contain 4 carbon atoms in a straight chain, is not satisfactory for conversion to maleic anhydride, although its presence is not harmful. In addition to butane, other saturated hydrocarbons within the scope of this invention include the pentanes, the hexanes, the heptanes, the octanes, the nonanes, the decanes or mixtures of any of these with or without butane. In addition to the saturated hydrocarbons, unsaturated hydrocarbons can be used. The preferred unsaturated hydrocarbon is butene, but other unsaturated hydrocarbons within the scope of this invention include butadiene, the pentenes, the hexenes, the heptenes, the octenes, the nonenes, the decenes or mixtures of any of these with or without butene. Cyclic compounds such as cyclopentane or cyclopentene or oxygenated compounds such as furan, dihydrofuran, or even tetrahydrofurfural alcohol are satisfactory. Furthermore, the aforementioned feed stocks are not necessarily pure substances, but can be technical hydrocarbons.

DESCRIPTION OF THE PREFERRED EMBODIMENTS

This invention is illustrated by, but not limited to, the following Examples, in which (except for Example 4 where there was no dehydration or conversion to a precursor prior to calcination) the description of the so-called "Catalyst Intermediate Preparation" includes not only the intermediate preparation but also the subsequent partial dehydration to the amorphous material which is suitable for conversion to the precursor.

EXAMPLE 1

Catalyst Intermediate Preparation 340 grams of vanadium pentoxide was added to an aqueous solution containing 466 grams of phosphoric acid in two liters of distilled water. The mixture was stirred for 8 hours to provide a yellow precipitate presumed to be a hydrate complex of vanadyl phosphate. An aqueous solution of hydrogen iodide [842 grams of 56.8%, 3.74 mole hydrogen iodide] was added slowly to the above creating the immediate formation of a green solution. Temperature of reaction was raised to reflux until all of the yellow solid was dissolved in about 30 minutes. The solution was cooled to 5° C. filtered through glass wool, removed from the precipitated iodine, washed twice with an excess of acetone and placed in 4 liters of distilled water for 48 hours at room temperature. By this time the resulting mixture contained a pasty blue mass partly light and partly dark blue. The mass was broken up and the mixture heated to reflux without stirring on a hot plate. Refluxing was continued for two hours. The product was suction filtered through two layers of Number 1 filter paper and dried over night at 125° C. The color was mostly gray with some pink.

Catalyst Precursor Preparation

This composition, which was the dehydrated intermediate comprising 25.55% vanadium, 15.33% phosphorus, and having a phosphorus vanadium atom ratio of 0.98, was charged in the amount of 260 grams to a 2 liter autoclave with 600 cc deionized water, and was heated to 150° C. for 4 hours. The autoclave was cooled to room temperature and the contents discharged onto a medium-porsity frit for vacuum filtration. The slurry was very thick and a green-gray color. A small quantity of soluble blue material was detected in the filtrate. The filtered material was dried at 120° C. over night with a final dry color of light green.

Catalyst Preparation 51 grams of the filtered material described above, in the form of 3/16×3/16" tablets were calcined in an oven. The temperature of the oven was raised to 375° C. during a period of two hours, and thereafter held at 375° C. for two hours. During the last 2½ hours, a stream of air was directed into the oven.

EXAMPLE 2

Catalyst Intermediate Preparation

The catalyst intermediate was prepared as in Example 1.

Catalyst Precursor Preparation 81.9 grams of the catalyst intermediate was charged to a 2 liter autoclave with 500 cc of dionized water. In order to obtain a phosphorus/vanadium atom ratio of 1.08, 3.14 grams of 99.4% phosphorus acid was added. The reactor was heated to 90° C. then raised to 150° C. with the vent closed, at which temperature it was held for one hour. It was then allowed to cool to 50° C. Contents of the reactor, a blue-green slurry, were discharged on to an evaporating dish and dried for 24 hours in an oven.

Catalyst Preparation

The recovered blue-green powder with a blue skin was ground to pass a number 18 screen, then pilled with graphite into 3/16" cylinders. These cylinders were calcined in air by heating them during a two hour period up to 400° C. and maintaining them at 400° C. for a period of six hours. During the last three hours of the six hours, air was permitted to enter the calcining autoclave.

EXAMPLE 3

Catalyst Intermediate Preparation 337.2 grams vanadium pentoxide was placed in a 500 ml flask with overhead trap to which 2,000 milliters deionized water and 462.2 grams of 85% phosphoric acid was added. The mixture was stirred at atmospheric pressure for three hours after which 835 grams of 56% hydroiodic acid was added dropwise and the mixture was permitted to stand overnight at room temperature. On the following day the reaction was heated to reflux temperature with dry ice being added to the trap. Refluxing was continued for 90 minutes, during which time iodine was being recovered in the trap. The slurry was washed twice with acetone, then filtered twice with an acetone wash in between. The slurry was dried over night in trays at 125° C., producing a dry material with a dark gray color.

Catalyst Precursor Preparation 500 grams of the dark gray material was placed in a two-liter stainless steel autoclave to which was added 19.17 grams of phosphorus acid and 100 ml of deionized water. Temperature was raised gradually to about 150° C., then permitted to lower gradually during the heating period of five hours. The blue-green catalyst precursor was dried in an oven at 125° C.

Catalyst Preparation

The catalyst precursor was tabletted as described above into 3/16" diameter tablets of an average length of 4.76 mm, and calcined on an open mesh stainless steel tray by raising the temperature of the tablets during a two hour period to 400° C., then holding the temperature of the tablets at 400° C. for a period of 6 hours. Air was introduced during the third hour and thereafter. 414.5 grams of yellow-green tablets were produced by the calcination.

EXAMPLE 4

Catalyst Intermediate Preparation 843 grams of vanadium pentoxide and 1155.5 grams of phosphoric acid were charged to a 12 liter flask with 5000 cc of deionized water. Over a period of 12 hours, the temperature of the flask was gradually raised to 95° C.; then lowered to 59° C. at which point the reflux condenser was removed and replaced with a cold trap. 2087 grams of hydrogen iodide was slowly added over a period of about two hours, and the reaction medium was stirred for several more hours while iodine was collected and the temperature maintained at about 95° C. The trap was filled with dry ice and a stream of $N_2$ gas was passed through the flask to force all $I_2$ into the trap. While the trap was periodically washed with water to remove $I_2$, additional hydrogen iodine was incrementally added until 2,087.5 grams had been added. Contents of the flask were cooled to room temperature, the liquid decanted therefrom, and the solid was washed with acetone and filtered three times, after which there was no trace of $I_2$ in the filtrate.

Catalyst Preparation

Without further treatment of the catalyst intermediate to obtain the catalyst precursor, 246 grams of the intermediate was mixed with 2.5 grams of powdered graphite and tabletted into 3/16" tablets which were then calcined by heating to 400° C. during a two hour period, and holding at 400° C. for a period of six hours. During the last five hours of the treatment, the catalyst was subjected to an air flow. The catalyst was yellow-brown in color.

EXAMPLE 5

Catalyst Intermediate Preparation

A 12 liter flask was charged with 1000 grams of vanadium pentoxide, 1370.7 grams of 85% phosphoric acid, and 5931 cc of deionized water. The mixture was stirred at room temperature for two hours during which the original orange color changed to yellow. After allowing to stand overnight, the mixture was heated to 45° C. and 2473.3 grams of hydrogen iodide (59% aqueous solution) was added drop wise with the evolved iodine collected in a trap over the flask. The mixture was heated to 95° C. and maintained thereabouts for six hours after which the flask was cooled to 85° C., disassembled and cooled further to about 30° C. Solids in the flask were removed, washed twice with acetone and filtered. The blue powder was air dried at room temperature. The residual solution from which solids were removed was refrigerated for five days at which time an additional quantity of blue solid material was filtered from the mixture. This blue solid was washed with acetone and filtered as above. The remaining filtrate was treated with acetone to precipitate a black wax which was removed from the mixture. The precipitate was again treated with acetone and filtered. This filtrate was a light blue material.

Preparation of Catalyst Precursor

A blend was prepared of the following components:
1010 g of the catalyst intermediate of Example 4
586 g of the blue powder described above just before refrigeration
309 g of the light blue powder described above immediately after removal of the black wax
850 g of the light blue powder described above after the last washing and filtration For a total of 2755 g which was heat treated for 24 hours at 125° C. to produce a partially dehydrated catalyst intermediate. 500 grams of this partially dehydrated catalyst intermediate was mixed with 49.4 grams of phosphorous acid and 1000 cc of deonized water which was heated to 145° C. and maintained at that temperature at 50-60 lbs. per square inch for 4.5 hours. The catalyst precursor was discharged onto a filter, vacuum filtered and washed with water.

Preparation of the Catalyst

The filter cake was broken into pieces and dried at 125° C. These pieces were ground to pass through a number 18 screen and formed into 3/16" tablets. The tablets were calcined by raising to a temperature of 400° C. during a period of two hours, and held at that temperature for six hours.

COMPARATIVE EXAMPLE 6

(typical of prior art)

The following components were charged to a five gallon autoclave:
3,217 grams of $V_2O_5$
2,039 grams of $H_3PO_4$
1,605 grams of $H_3PO_3$
10,882 grams of distilled water The contents of the autoclave were heated to 148° C., which temperature was maintained for four hours after which the autoclave was cooled to 68° C.; then placed on a steam bath and taken to dryness. The catalyst was formed into 3/16th inch diameter tablets. The tablets were calcined at 500° C. for eight hours in air.

TABLE I

CATALYST PERFORMANCE DATA: 3/16" TABLETS, 1.5% BUTANE, 1450 $HR^{-1}$ S.V.

| Example No. | Tube Length, Ft. | Bath Temp., °C. | Conversion, % | Selectivity, % | Theory Yield, % |
|---|---|---|---|---|---|
| 1 | 0.5 | 356 | 79.0 | 64.4 | 50.8 |
| 2 | 0.5 | 405 | 78.8 | 67.4 | 53.0 |
| 3 | 4.0 | 404 | 78.9 | 69.3 | 54.4 |
| 4 | 0.5 | 450 | 62.2 | 21.5 | 13.4 |
| 5 | 4.0 | 367 | 79.8 | 72.2 | 57.6 |
| Comp. Ex. 6 | 4.0 | 405 | 76.3 | 59.3 | 45.2 |

Catalyst prepared from each of the examples were employed in the same maleic anhydride production reactor described above, the only variance being in the length of the reactor tube which is specified in Table I. A conversion rate of 79 was sought in each case, and the temperature of the bath controlling the reaction temperature was measured in each case so as to provide comparative data.

It will be noted that some of the date obtained through the new catalyst intermediate of this invention does not reflect an improvement over the prior art. Example 4 is in fact considerably worse. Example 4 illustrates the fact that it is necessary to convert the intermediate of this invention to a precursor before calcining. Examples 2 and 3, showing only a slight improvement over Example 6, illustrate only partial recovery of a pure intermediate and only partial conversion to a pure precursor. Examples 1 and 5 are typical of improvements which can now be obtained through the knowledge of the unsuccessful experiments shown.

We claim:
1. A method for the preparation of maleic anhydride from butane comprising reacting an oxygen-containing gas and butane at a temperature between about 350° and 600° C. in the presence of the product of the process comprising:
   (1) forming a first reaction product from a vanadium compound and a phosphorus compound having a phosphorus-to-vanadium atom ratio of 0.8–1.5:1
   (2) reacting the first reaction product with hydrogen iodide to form a catalyst intermediate;
   (3) partially dehydrating the catalyst intermediate to yield an amorphous material;
   (4) heating the amorphous material in an aqueous environment at a temperature of about 120°–250° C. to form a catalyst precursor and
   (5) calcining the catalyst precursor at about 300°–600° C. to form the catalyst.

2. The catalyst of claim 1 wherein the vanadium compound is vanadium pentoxide.

3. The catalyst of claim 1 wherein the phosphorus compound is phosphoric acid.

4. The method of claim 1 wherein the vanadium compound is vanadium pentoxide and the phosphorus compound is phosphoric acid.

5. The method of claim 1 wherein the temperature of (3) is 145°–150° C.

6. A method for the preparation of maleic anhydride from butane comprising reacting an oxygen-containing gas and butane at a temperature between 350° C. and 600° C. in the presence of the product of the process comprising:
   (1) partially dehydrating a catalyst intermediate comprising phosphorus, vanadium, hydrogen and oxygen having major X-ray diffraction peaks of about:

d-spacing
   7.45
   6.52
   4.20
   4.04
   3.20
   2.87
   2.80 to yield an amorphous material
   (2) heating the amorphous material in an aqueous environment at a temperature of about 120°–250° C. to form a catalyst precursor and
   (3) calcining the catalyst precursor at about 300°–600° C.

* * * * *